US012758488B2

(12) United States Patent
Saigal et al.

(10) Patent No.: US 12,758,488 B2
(45) Date of Patent: Oct. 13, 2026

(54) TRANSDURAL DRUG DELIVERY SYSTEM

(71) Applicants: University of Washington, Seattle, WA (US); The Regents of the University of California, Oakland, CA (US)

(72) Inventors: Rajiv Saigal, Seattle, WA (US); Jessica Johnson, Seattle, WA (US); Tianyu Zhao, Seattle, WA (US); Maximilian Walter, Seattle, WA (US)

(73) Assignees: University of Washington, Seattle, WA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 17/744,333

(22) Filed: May 13, 2022

(65) Prior Publication Data

US 2022/0401355 A1 Dec. 22, 2022

Related U.S. Application Data

(60) Provisional application No. 63/188,292, filed on May 13, 2021.

(51) Int. Cl.
*A61K 9/00* (2006.01)
*A61K 31/573* (2006.01)
*A61M 37/00* (2006.01)

(52) U.S. Cl.
CPC .......... *A61K 9/0021* (2013.01); *A61K 31/573* (2013.01)

(58) Field of Classification Search
CPC .. A61K 9/0021; A61K 31/573; A61K 9/0085; A61M 2037/0023; A61M 2037/0046; A61M 2037/0053; A61M 2037/0061
See application file for complete search history.

(56) References Cited

U.S. PATENT DOCUMENTS

2005/0209565 A1* 9/2005 Yuzhakov ......... A61M 37/0015 604/173
2006/0073182 A1 4/2006 Wong et al.
2007/0179428 A1* 8/2007 Kralick, D.O. ...... F16K 99/0028 604/9
2012/0064142 A1 3/2012 Pillay et al.
2013/0237960 A1* 9/2013 Pettis .................. A61M 5/3286 604/117
2015/0197484 A1* 7/2015 Stinchcomb ............ A61P 25/08 514/420
2018/0064920 A1* 3/2018 Desimone .............. B33Y 80/00

FOREIGN PATENT DOCUMENTS

WO 2012138854 A1 10/2012

OTHER PUBLICATIONS

Oh et al (A novel microneedle array for the treatment of hydrocephalus). Micosyst Technol (2014) 20:1169-1179. (Year: 2014).*
Boehler, C., et al., "Actively controlled release of Dexamethasone from neural microelectrodes in a chronic in vivo study," Biomaterials, vol. 129, 2017, pp. 176-187.
Kallinteri, P., et al., "Novel Functionalized Biodegradable Polymers for Nanoparticle Drug Delivery Systems," Biomacromolecules, vol. 6, No. 4, 2005, pp. 1885-1894.
Ludvig, N., et al., "An implantable triple-function device for local drug delivery, cerebrospinal fluid removal and EEG recording in the cranial subdural/subarachnoid space of primates," Journal of Neuroscience Methods, vol. 203, 2012, pp. 275-283.
Wang, Y., et al., "IEffective improvement of the neuroprotective activity after spinal cord injury by synergistic effect of glucocorticoid with biodegradable amphipathic nanomicelles," Drug Delivery, vol. 24, No. 1, Feb. 6, 2017, pp. 391-401.

* cited by examiner

*Primary Examiner* — Mina Haghighatian
(74) *Attorney, Agent, or Firm* — Bozicevic, Field & Francis LLP; Edward J. Baba; Mandar A. Joshi

(57) ABSTRACT

Devices for and related methods of treating a subject having a neurological injury to prevent or mitigate secondary injury are described. In an example, the devices include a base and a plurality of microneedles protruding from the base, the microneedles including a biocompatible and biodegradable matrix, and a neurologically active ingredient disposed within the matrix. In an example, a portion of the plurality of microneedles is shaped to penetrate the dura when the device is placed in contact with the dura.

24 Claims, 8 Drawing Sheets

2mm height on 2mm base

4mm height needles densley packed

4mm height needles sparse

"The X" (4mm)

TRANSDURAL DRUG DELIVERY SYSTEM

CROSS-REFERENCE TO RELATED APPLICATION

This application claims the benefit of U.S. Provisional Application 63/188,292, filed May 13, 2021, the entire disclosure of which is hereby incorporated by reference.

BACKGROUND

In the United States, the incidence rate of spinal cord injury (SCI) is approximately 54 cases per million, resulting in 17,900 new cases per year. Currently, about 296,000 persons are living with SCI. The cost of living with SCI depends on the severity level, with AIS D scores costing $379,698 initially then $46,119 every subsequent year. A 25-year-old patient that suffers a minor SCI injury can expect to pay $1,724,594 over their lifetime in medical costs directly related to the injury. This number rises as higher forms of paralysis occur, with a high tetraplegic patient paying $1,163,425 in their first year after injury and paying $202,032 every subsequent year. A 25-year-old patient suffering a high tetraplegic injury has a lifetime cost of $5,162,152.

Traumatic spinal cord and brain injuries may lead to a devastating loss of neurological function. After the traumatic, primary insult, a secondary injury phase ensues, which significantly increases the extent of the injury. Inflammation is a dominant component of secondary injury, which includes the immune response in which free radicals and proinflammatory cytokines are released that induce the death of surrounding neurons. Dexamethasone, a corticosteroid, produces neuroprotective effects by inhibiting inflammation and reducing cytokine release. However, the clinical application of large systemic doses of steroids is limited by side effects, such as sepsis and pneumonia.

Clinically, systemic doses of steroids have shown anti-inflammatory effects that reduce the secondary injury phase at the injury site. With large dosages circulating the body, there are many side effects such as pneumonia, sepsis, or hypoglycemia. Therefore, a localized delivery method could provide therapeutic results with minimal side effects. One of the most clinically used steroids for this treatment is dexamethasone. A dosage of 8 μg/mL over a 24-48 hour window has shown improvement in reducing inflammation in activated microglial cells.

The field of transdermal microneedle arrays is rapidly growing. Microneedle patches allow for localized drug delivery with applications for burn victims, child vaccinations, and diabetic patients. To date, there are no known applications of microneedles for transdural drug delivery. Thus, there is a need to develop a localized delivery method that minimizes these side effects and improves efficacy by delivering directly at the injury site.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides a device including a base, and a plurality of microneedles protruding from the base, the microneedles comprising a biocompatible and biodegradable matrix, and a neurologically active ingredient disposed within the matrix is disclosed.

In another aspect, the present disclosure provides a method of making a microneedle device, the method including disposing a neurologically active ingredient and a monomer mixture in a microneedle mold; and polymerizing the monomer mixture in the microneedle mold to provide microneedles comprising a biocompatible and biodegradable matrix encasing the neurologically active ingredient is disclosed.

In yet another aspect, the present disclosure provides a method of treating a subject having a neurological injury to prevent or mitigate secondary injury, the method including applying a microneedle device to dura of the subject at or adjacent to a site of the neurological injury, the microneedle device comprising a base, and a plurality of microneedles protruding from the base, the microneedles including a biocompatible and biodegradable matrix, and a neurologically active ingredient disposed within the matrix, where applying the microneedle device to the dura pierces the dura, thereby releasing the neurologically active ingredient to injured neural tissue of the subject is disclosed.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

Figure 1B:
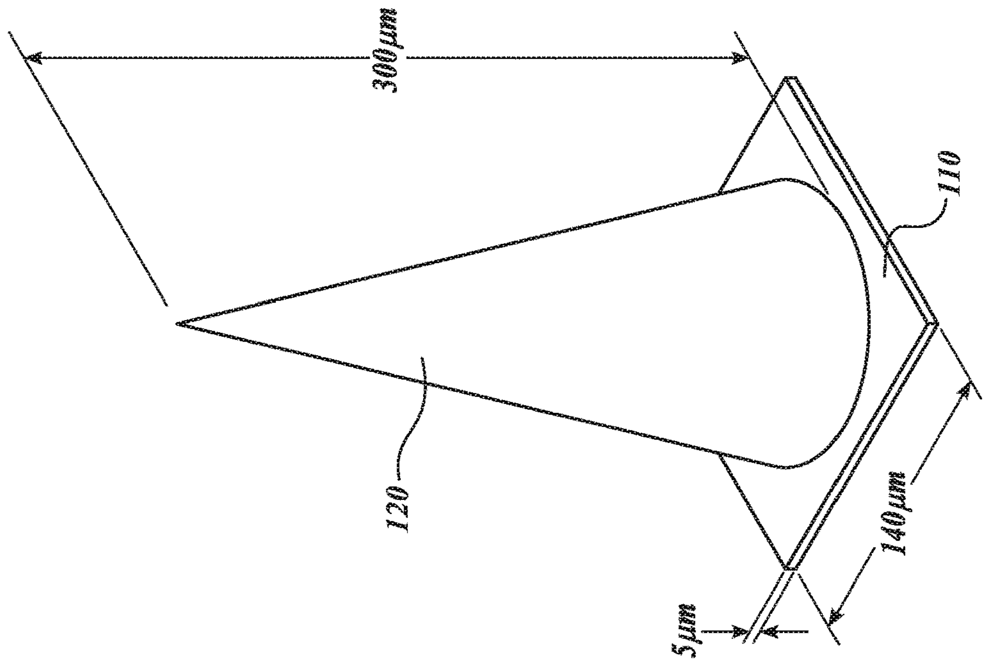
FIG. 1B is an example microneedle of the device of FIG. 1A, in accordance with the present technology.

While illustrative embodiments have been illustrated and described, it will be appreciated that various changes can be made therein without departing from the spirit and scope of the invention.

Described herein are a drug delivery device and method to provide a neurologically active ingredient directly to the location of injury in a microneedle format.

Also described herein is a localized drug delivery method for the treatment of traumatic spinal cord injury. The goal was to improve drug delivery to the injury site post-injury that reduces the need for systemic dosing of steroids and their detrimental side effects. A secondary goal was to reduce the extent of the secondary injury phase by reducing the presence of proinflammatory cytokines and the release of nitric oxide from microglial cells. Described herein is the process to achieve these goals with a polymer hydrogel system to encapsulate a model drug, dexamethasone. In one embodiment, the approach is to manufacture microneedle arrays formulated out of this hydrogel. In an embodiment, the microneedles are configured to pierce the dura and deliver a drug to the subdural space without the need to open the dura. To properly quantify dexamethasone release, a liquid chromatography-mass spectrometry method was developed that allowed for the accurate analysis of samples. Finally, these systems were evaluated using a novel transwell insert that simulated the ability to deliver drugs across a membrane and into the subdural space.

Ultraviolet-visible absorption spectroscopy is a prevalent method to quantify a wide variety of molecules. It has inexpensive and quick operation without extensive sample preparation before receiving results. UV-Vis works by emitting light within the UV to visible light spectrum through the sample, and then a sensor measures the amount of light transmitted (T). Using formula 1, the absorbance (A) of the sample can be calculated. Using Beer's Law, the concentration of the sample can be determined. Comparing the results to a known, linear standard curve, the unknown concentration of the sample can be computed. This method can be helpful when samples include very distinct analytes that have different absorbances. This method struggles when the sample matrix has a variety of chemicals that may have similar structures. To help separate the absorbances, an analyte such as dexamethasone can be fluorescently tagged to distinguish it from the rest of the matrix.

$$A=-\log(T) \qquad \text{Equation 1: Transmittance to Absorbance}$$

Liquid Chromatography coupled mass spectrometry (LCMS) is a highly robust system for quantifying the amount of analyte in solution. It uses two different techniques, first separating different compounds from solution using liquid chromatography. In this phase, the samples are mixed with a gradient of solvents; usually, one is aqueous, and the other is organic. This solution is then run through an HPLC column wherein the molecule's physical and chemical attributes determine its affinity to the column and determine the speed at which it travels through the column. This separation allows molecules with similar absorbance or structure to be quantified using MS or UV-Vis at varying times.

After the sample is separated, it can then be quantified using the MS. This is done by a process known as electrospray ionization. The machine charges the solution in a capillary tube which charges individual droplets. These droplets are then sprayed through a sensor and as they land on and evaporate, they impart a charge onto the sensor. From this, a mass to charge ratio (m/z) can be measured. The MS machine may also include a collision gas, argon, which is added into the stream that causes the molecules to fragment, introducing daughter ions that can also quantify to help determine a specific analyte.

The machine outputs a chromatogram which includes time on the horizontal axis. The retention time of a specific molecule, such as dexamethasone, should remain consistent across all trials. The intensity of the signal is on the vertical axis. The area under the curve can then be solved to understand total intensity at a given time point. When compared to a standard linear curve, the concentration of analyte in the solution can be determined.

Microglial cells are a type of macrophage cell located within the central nervous system (CNS). Their primary role is to remove dead or diseased neurons within the CNS. Microglial cells are one of the primary drivers of the inflammatory response present after traumatic injury. They release nitric oxides and cytokines that drive inflammation within the tissue. Because of these properties, they can be used as the cell lines within in-vitro studies.

Nitric Oxide (NO) is naturally produced by the CNS and is used for several cellular functions. In the CNS, it helps with cognitive function, maintenance of the synapsis, and other bodily functions. Microglia cells, when under stress, produce excess NO, which becomes toxic to the surrounding neurons. This excess causes cells to become cytotoxic and undergo apoptosis. Because of NO's role in progressing the secondary injury phase, it was chosen as a marker to determine the decrease in inflammation within the in-vitro model.

Cytokines are a type of protein secreted by cells as a signaling agent. They have many functions, but a primary factor of cytokine production is to elicit an inflammatory response. In the CNS, interleukins (IL) and tumor necrosis factor (TNF) are overproduced when the tissue is damaged. This leads to inflammation within the tissue and drives many neurons to cell death. For these studies, the system's ability to reduce IL-1b, IL-6, TNF-α, and MCP-1 was analyzed, as these have been linked as crucial cytokines in the inflammation immediately post-injury.

A motivation for the present technology is to reduce the secondary injury phase by localizing the delivery of anti-inflammatory steroids directly to the injury site. To address this motivation, a biodegradable microneedle array was developed. In an embodiment, the array is configured to pierce or penetrate the dura when applied thereto and deliver a composition, such as a steroid, into the subdural space directly at the injury site. In an embodiment, the microneedle array comprises a biodegradable polymer that provides a controlled release for 24-72 hours and maintain a level of 8 μg/mL of dexamethasone. As discussed further herein, a polymer matrix according to an embodiment of the present disclosure achieves this target window was developed.

In one aspect, the present disclosure provides a device including a base, and a plurality of microneedles protruding from the base, the microneedles comprising a biocompatible and biodegradable matrix, and a neurologically active ingredient disposed within the matrix is disclosed.

Figure 1A:
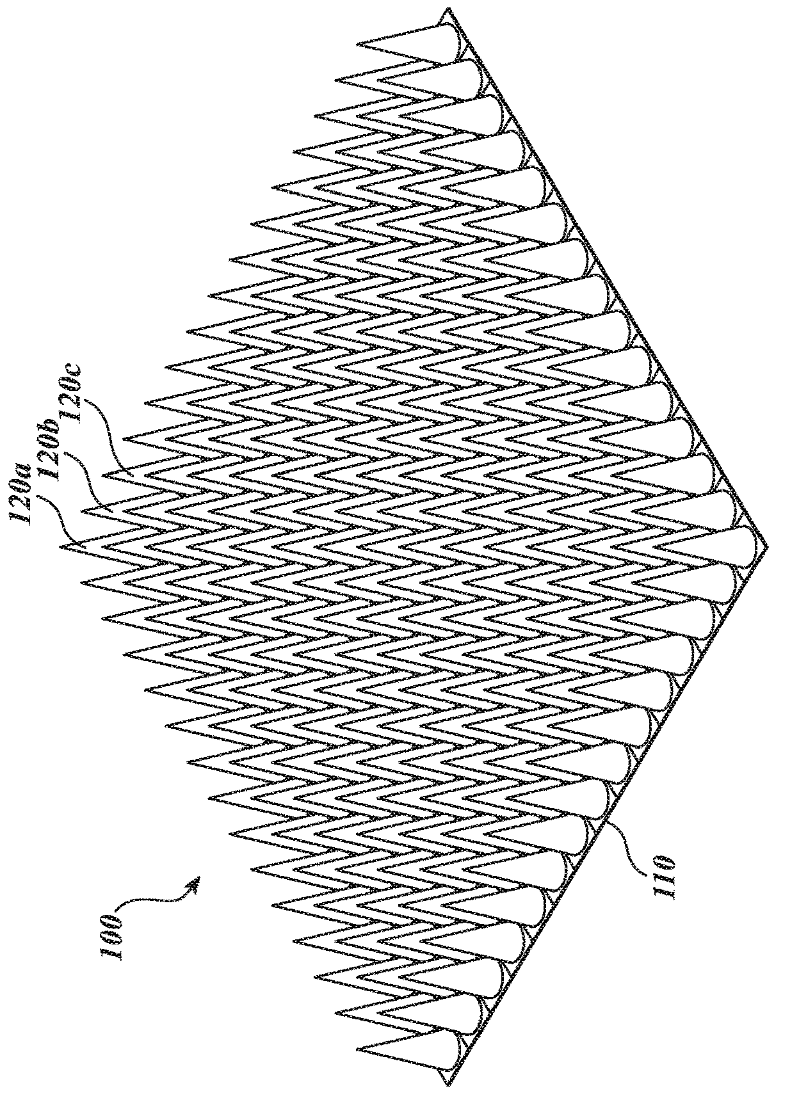
FIG. 1A illustrates a schematic view of an example device, in accordance with the present technology.

FIG. 1A is an example device 100, in accordance with the present technology. In the illustrated embodiment, the device 100 includes a base 110, and a plurality of microneedles 120*a*, 120*b*, 120*c* protruding from the base 110. As shown, microneedles 120 of the plurality of microneedles 120*a*, 120*b*, 120*c* are disposed on the base 110 in an array. In some embodiments, the microneedles 120*a*, 120*b*, 120*c* are made of or otherwise comprise a biocompatible and biodegradable matrix, and a neurologically active ingredient disposed within the matrix. As described herein, an active ingredient is disposed within the matrix of the microneedles, as opposed to coated on the microneedles

120*a*, 120*b*, 120*c*. Further, as described herein, the device 100 is not connected to a voltage source of an electrical potential source. In some embodiments, the neurologically active ingredient is an anti-inflammatory compound. In some embodiments, the neurologically active ingredient is a corticosteroid.

The microneedle design may take any number of forms. In some embodiments, the size of the microneedle is configured for in-vivo work in rodents. In some embodiments, the size of the microneedle is shaped or otherwise configured for in-vivo work in humans.

In some embodiments, a portion of the plurality of microneedles 120*a*, 120*b*, 120*c* is shaped to penetrate the dura when the device is placed in contact with the dura. This allows for the benefit of being able to deliver the drug into the intradural, subdural, subarachnoid, or intramedullary space.

In one embodiment, the device 100 is an array of 15×15 conical needles 120*a*, 120*b*, 120*c*, such as illustrated in FIG. 1A, each with a height of 300 nm and a base diameter of 100 nm, sat on top of a 200 nm base layer 110 that connected the array. In some embodiments, a center point of each needle 120*a*, 120*b*,120*c* is 300 nm away from the center point of the neighboring needle. In some embodiments, the design of the device 100 produces an array configured to pierce the dura substitute and deliver a correct payload. In some embodiments, the needles 120*a*, 120*b*, 120*c* are conical and have a height ranging from 0.5-5 mm, and a consistent base diameter of 1 mm.

In some embodiments, the needles 120*a*, 120*b*, 120*c* sit on top of a base layer 110 with a height of 1 mm. In some embodiments, such as shown in FIGS. 7A-7D, spacing is varied with arrays of 5×5 or sparse arrays with only a single needle 120 on all four corners of the base layer 110.

In operation, the plurality of microneedles 120*a*, 120*b*, 120*c* is configured to pierce the dura (not pictured in FIG. 1A) when applied thereto.

FIG. 1B is an example single microneedle 120, in accordance with the present technology, and is an example of one of the plurality of microneedles 120*a*, 120*b*, or 120*c* illustrated in and discussed further herein with respect to FIG. 1A. In some embodiments, the microneedles 120 of the plurality of microneedles 120*a*, 120*b*, 120*c* have a length extending from the base in a range of about 50 μm to about 2000 μm.

In another aspect, the present disclosure provides a method of making a microneedle device. In an embodiment, the method includes disposing a neurologically active ingredient and a monomer mixture in a microneedle mold; and polymerizing the monomer mixture in the microneedle mold to provide microneedles comprising a biocompatible and biodegradable matrix encasing the neurologically active ingredient is disclosed. In some embodiments, the monomer mixture includes monomers selected from the group consisting of ethylene glycol, acrylic acid, vinylpyrrolidone (VP), and combinations thereof.

To achieve a biodegradable microneedle device 100 configured to pierce the dura, in some embodiments, the microneedle 120 comprises a hydrogel mixture. Specifically, poly(ethylene glycol) diacrylate (PEG-DA) may be used to encapsulate different drugs and provided the structural support to pierce the dermis. In one example, PEG-DA was mixed with a cross-linking agent VP. This solution was then polymerized under ultraviolet light to create a polymer network that encapsulates the neurologically active ingredient, such as dexamethasone.

In some embodiments, the hydrogel mixture is a mixture of poly(ethylene glycol) diacrylate (PEG-DA), poly(vinylpyrrolidone) (PVP), Irgacure™, poly(lactic co-glycolic acid) (PLGA), poly(caprolactone) (PCL), poly(vinyl alcohol), poly(pyrrole), poly(3,4-ethylenedioxythiophene) polystyrene sulfonate (PEDOT), and combinations thereof. In some embodiments, the hydrogel mixture is a monomer solution. In an embodiment, the hydrogel mixture is a mixture of PEG-DA, and PVP. In some embodiments, the neurologically active ingredient is selected from the group consisting of IL-10, dexamethasone, methylprednisolone, hydrocortisone, riluzole, minocycline, brain derived neurotrophic factor (BDNF), nerve growth factor (NGF), neurotrophin-3 (NT-3), and combinations thereof. In some embodiments, a weight:weight ratio of the neurologically active ingredient to the matrix is in a range of between about 80:15 and 95:5.

In some embodiments, the solution for the microneedles 120 is created as a polymer mixture of VP and/or PVP and PEG-DA. This polymer solution can be polymerized under UV light using the photo initiator, irgacure2959™, which causes the VP and/or PVP to begin cross-linking with itself and the PEG-DA molecules, making a dense network that can be used to encapsulate a neurologically active ingredient, such as dexamethasone.

The hydrogel solution may be prepared in a 95/5 w/v ratio of VP to PEG-DA. 1.018 mL VP, 312.5 μL PEG-DA-700, 9.38 mg of irgacure2959™, and 469 uL of PBS were added to a 15 mL falcon tube (Table 1). The tube may be covered in aluminum foil and vortexed for 1 minute. The tube may then be stored in a 2° C. refrigerator.

TABLE 1

Volumes of chemicals used to create VP-PEG-DA solution.

| | Molecular Weight (g/mol) | Ratio | Moles (mol) | Weight (g) | Volume (μL) |
|---|---|---|---|---|---|
| VP | 111.14 | 95 | 0.0095 | 1.0583 g | 1018 |
| PEGDA700 | 700 | 5 | 0.0005 | 0.35 g | 312.5 |
| Irgacure2959 | | | | .00938 g | |
| PBS | | | | .469 g | 469 |

In one example, the dexamethasone-loaded solution was prepared by adding 200 μL of VP to 20 mg of dexamethasone in a 5 mL Eppendorf tube. The solution was vortexed for 1 minute. 2 mL of VP-PEG-DA solution was added to the tube and vortexed for 1 minute. The tube was then covered in aluminum foil and stored in the refrigerator.

Initial testing of the gel produced excellent results from the microneedle formats. The release was consistent and surpassed the 8 μg/mL goal of the project. With these results, the transdural release mechanism was developed.

FIGS. 2A-2D are illustrations of example process steps for manufacturing an example device, in accordance with the present technology. In some embodiments, to fabricate the microneedles, a three-stage molding process is employed. In some embodiments, the device 100 is made by disposing a neurologically active ingredient and a monomer mixture in a microneedle mold and polymerizing the monomer mixture in the microneedle mold to provide microneedles comprising a biocompatible and biodegradable matrix encasing the neurologically active ingredient. As described herein, the neurologically active ingredient is disposed in the matrix, as opposed to coated on the microneedles.

As illustrated, the process includes a three-stage molding technique. A positive mold of the microneedle array is created using 3D printing tools and is then cast into polydimethylsiloxane (PDM) to create a negative mold. With this mold, the monomer-drug solution can be vacuum loaded in and cured under UV light. This mold may be re-usable and has been shown to sustain over 50+ castings before mechanical failure.

Figure 2A:
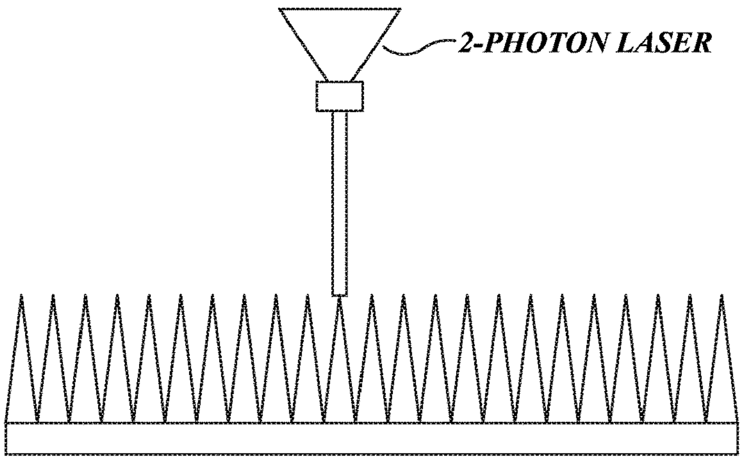
FIGS. 2A-2D are schematic illustrations of example process steps for manufacturing an example device, in accordance with the present technology.

FIG. 2A illustrates the process of manufacturing a positive mold. In some embodiments, the device is made by additively manufacturing a negative mold shaped to form a negative space of the microneedle mold and disposing the negative mold in an elastomer to form the microneedle mold. 3D printers may be used to make the positive molds, as this gives flexibility to change design quickly compared to milled or prefabricated metal molds. In some embodiments, the positive microneedles are fabricated using a three-dimensional photolithography tool, such as Nanoscribe™ (Nanoscribe, Gmbh). The machine uses a two-photon polymerization laser to polymerize IP-S resist on a plasma-treated silicon wafer. The microneedles may be printed in an array format, such as in a 15×15 array. The dimensions of the conical needles may be 300 μm in height with a 100 μm diameter base. These dimensions allow the microneedles to pierce or penetrate the dura. In some embodiments, the microneedle mold defines a plurality of structures shaped to form the plurality of microneedles. In some embodiments, the plurality of structures defines a depth in a range of about 50 μm to about 2000 μm.

The needles may be printed on a 50 μm base layer with a center to center spacing of 140 μm. After polymerization, the needles may be developed in SU-8 Developer for 20 minutes. In some embodiments, needles are then cleaned with isopropanol solution to remove any un-exposed IP-S resist.

Figure 2B:
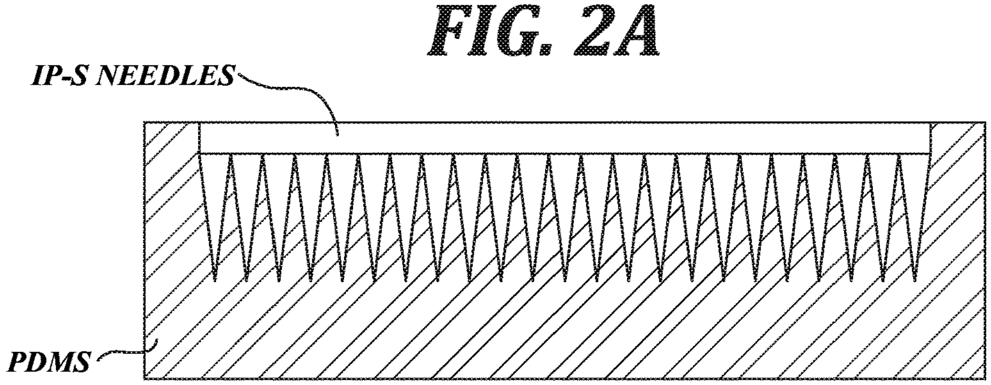

FIG. 2B illustrates the process of casting the positive mold to form a negative mold. After the initial design is printed, it may be cast. After curing, this negative mold may be vacuum loaded with the monomer solution and cured under UV light. The resulting polymer array may be extracted from the mold and used for experimental testing. In some embodiments, the positive molds are cast into polydimethylsiloxane (PDMS).

In one example, the silicon wafer is placed into a small container made of aluminum foil. A 10:1 ratio of PDMS base polymer solution was mixed with a curing agent (SYLGARD184, DOW). For this application, 10 g of the base were mixed with 1 g of curing agent. The resulting mixture was mixed for 5 minutes and placed into a vacuum chamber for 10 minutes to remove any bubbles. The mixture was then poured into the foil container until the entire array was covered with 4-5 mm of mixture. The container was then placed into the vacuum chamber for 10 minutes to remove any air bubbles. The container was then placed into an oven for 2 hours at 80° C.

Figure 2C:
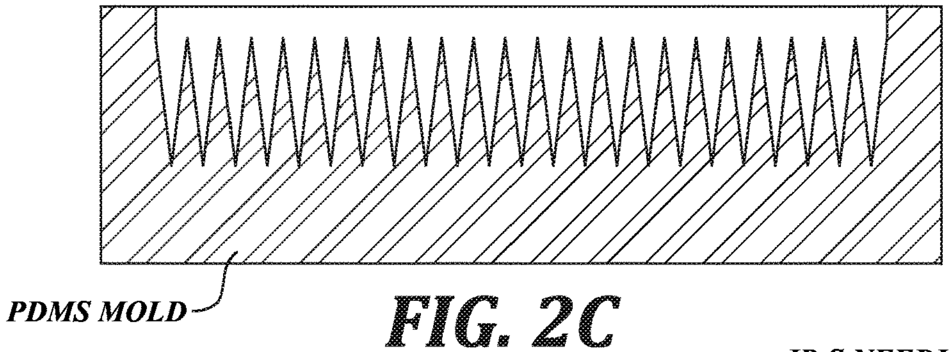

FIG. 2C is an illustration of the resulting PDMS mold. In some embodiments, the mold is cooled, and the foil is removed. The silicon wafer may be gently peeled from the PDMS mold, making sure not to leave any positive microneedles in the mold.

Figure 2D:
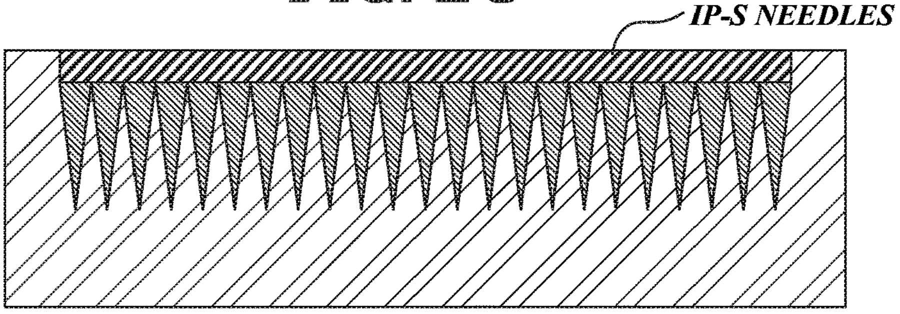

Finally, in FIG. 2D, the device is formed, as described herein. With the negative mold complete, the polymer can be loaded. In some embodiments, 10 uL of VP-PEG-DA monomer solution is pipetted onto the mold and placed into the vacuum chamber for 5 minutes. The mold may then be inspected under the microscope to verify that all microneedle wells are filled with monomer solution. The mold may then be placed in a foil-wrapped glass dish. A small Kimwipe may soaked in DI water and put into the dish, and a glass lid may be placed onto the container. The dish can then be placed under UV light. In one embodiment, the light emits UV light with a wavelength of 365 nm for 30 minutes. After curing, the polymer microneedle array may be carefully removed from the mold using forceps and stored in an Eppendorf tube.

In some embodiments, for features larger than 350 μm, a UV resin printer may be used to print positive molds (ASIGA, MAX UV). In one example, this printer had a resolution of 24 μm per layer. The printer used 385 nm UV light to polymerize a proprietary monomer solution (PlasCLEAR, ASIGA). After printing, the print was placed into an isopropanol bath for 5 minutes to remove any uncured resin. The array was then cured under 6000 flash cycles of UV in the range of (300 nm-700 nm). This method was used to print an array with conical needles ranging from 0.5-5 mm in height and a base diameter of 1 mm on top of a base layer of 1 mm height.

Figure 3A:
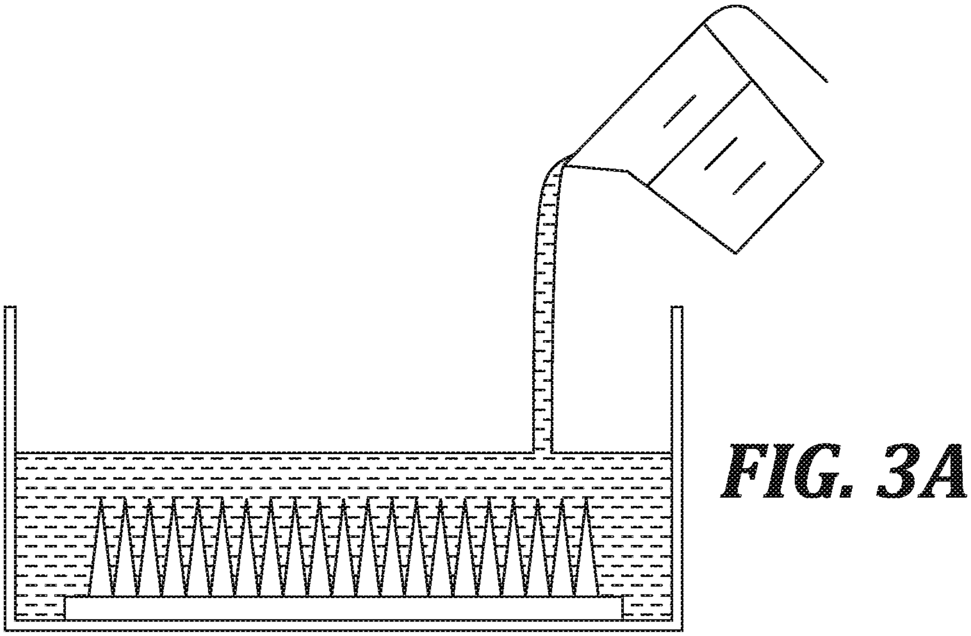
FIGS. 3A-3C are schematic illustrations of example process steps for manufacturing a device, in accordance with the present technology.
Figure 3B:
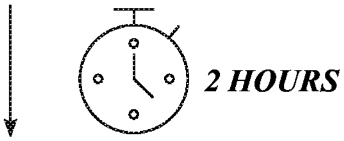
Figure 3B:
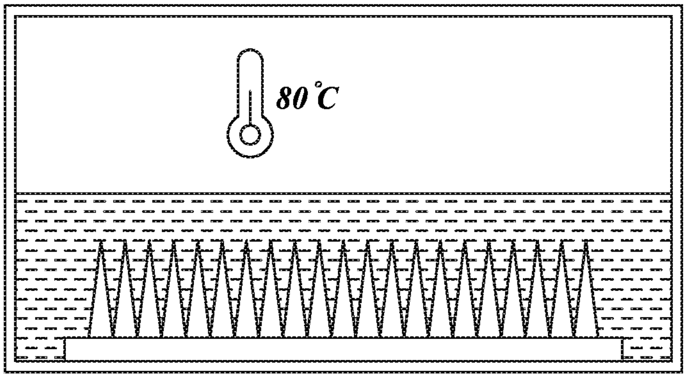
Figure 3C:
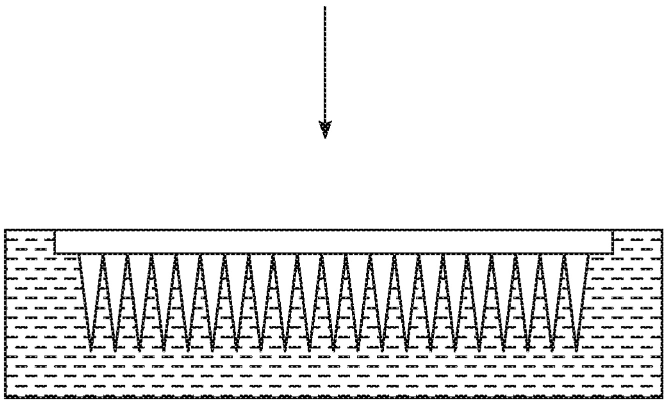

FIGS. 3A-3C are illustrations of example process steps for manufacturing a device, in accordance with the present technology. Illustrated in FIGS. 3A-3C is the PDMS molding process. First, in FIG. 3A the solution may be poured over the molds. Second, in FIG. 3B the container may be placed into an oven for 2 hours at 80° C. Finally, in FIG. 3C the positive mold is removed.

The device may be formed by loading the mold with a monomer and/or polymer solution. The vacuum chamber may be adequate for loading the monomer solution, but there may be issues with more viscous solutions, as there is not enough force to consistently load each microneedle well. The arrays were examined at various stages in a mold's lifecycle to evaluate the consistency. In some embodiments, the tips of the needles start to thin out or break off There may also be a slight curve in the needles, which may be caused by the extraction of the arrays from the mold. To avoid this, in some embodiments, all arrays were extracted vertically and not at an angle.

Overall, the final manufacturing system is efficient and can produce multiple polymer microneedle arrays. During the development of the system, it was found that printing microneedles onto quartz wafers caused poor adhesion. This would cause microneedles to come off the slide while printing and during the PDMS molding stage. There were also issues with the slide surface being unlevel, which caused prints to fail. These issues were resolved by refining the print method and switching to a silica wafer. These changes allow for better adhesion to the slide, allowing up to five negative PDMS molds to be made.

In another aspect, a method of treating a subject having a neurological injury to prevent or mitigate secondary injury, including applying a microneedle device to dura of the subject at or adjacent to a site of the neurological injury, the microneedle device comprising a base and a plurality of microneedles protruding from the base, the microneedles including a biocompatible and biodegradable matrix, and a neurologically active ingredient disposed within the matrix, where applying the microneedle device to the dura pierces the dura, thereby releasing the neurologically active ingredient to injured neural tissue of the subject is described.

Example #1

Described herein is the process of developing a high-throughput HPLC-MS method for the quantification of dexamethasone from a variety of mediums. A Waters Quattro Micro quadrupole tandem mass spectrometer was used with a 1525 u LC pump and a 2777 autosampler. For LC separation, a Zorbax Extended C-18 μm HPLC column from Agilent was used. The final method uses 1% Acetic Acid/5% Acetonitrile/94% $H_2O$ for mobile phase A and methanol for mobile phase B. Argon gas was used as the collision gas with nitrogen gas used in the cone.

TABLE 2

Mobile phase gradient for LC-MS method.

| Time (min) | Flow (ml/min) | % A | % B | Curve |
|---|---|---|---|---|
| 0 | 0.2 | 70 | 30 | |
| 4 | 0.2 | 5 | 95 | 6 |
| 6.5 | 0.2 | 5 | 95 | 6 |
| 7 | 0.2 | 70 | 30 | 6 |

The total run time was 10 minutes, and the analyte retention time was found to be 3.71 minutes.

The MS was tuned with a capillary voltage of 3.5 kV, cone voltage of 22V, extractor at 3V, and RF lens set to 0.2V. Source temperature was set to 100° C. and desolvation temperature to 350° C. Parent peak was set at 393.2 with a daughter peak of 373.5. Parent scan was set to 56 and a mass of 288.21, a span of 1, and a gain of 1. The daughter scan was set to 288.3, with a mass of 172.3, a span of 1, and a gain of 6.

Before each run, the machine was tested by running standard five and evaluating the peak of previous runs. The start of each run was the standard curve in ascending order. A MeOH wash sample was run before and after each standard curve. Samples were run in groups. All samples from a variable at a given time point were run, followed by a MeOH wash. After all groups in a time point were run, the standard curve was rerun to monitor drift. After all samples were run, the standard curve was rerun.

Switching to LC-MS provided a more accurate system of quantification compared to UV-Vis. Early methods included ammonium acetate for mobile phase A, which caused precipitation during the run, causing the system to shut down due to overpressure. This was resolved by switching to the 1% AA/5% ACN/94% $H_2O$ mobile phase A. This method can be used for various mediums such as PBS and future in-vivo work with processed tissue samples. The system can be improved by including an internal standard to each sample, such as flumethasone. Flumethasone has a very similar chemical structure and can account for any loss during the processing and quantification of the samples.

Figure 6:
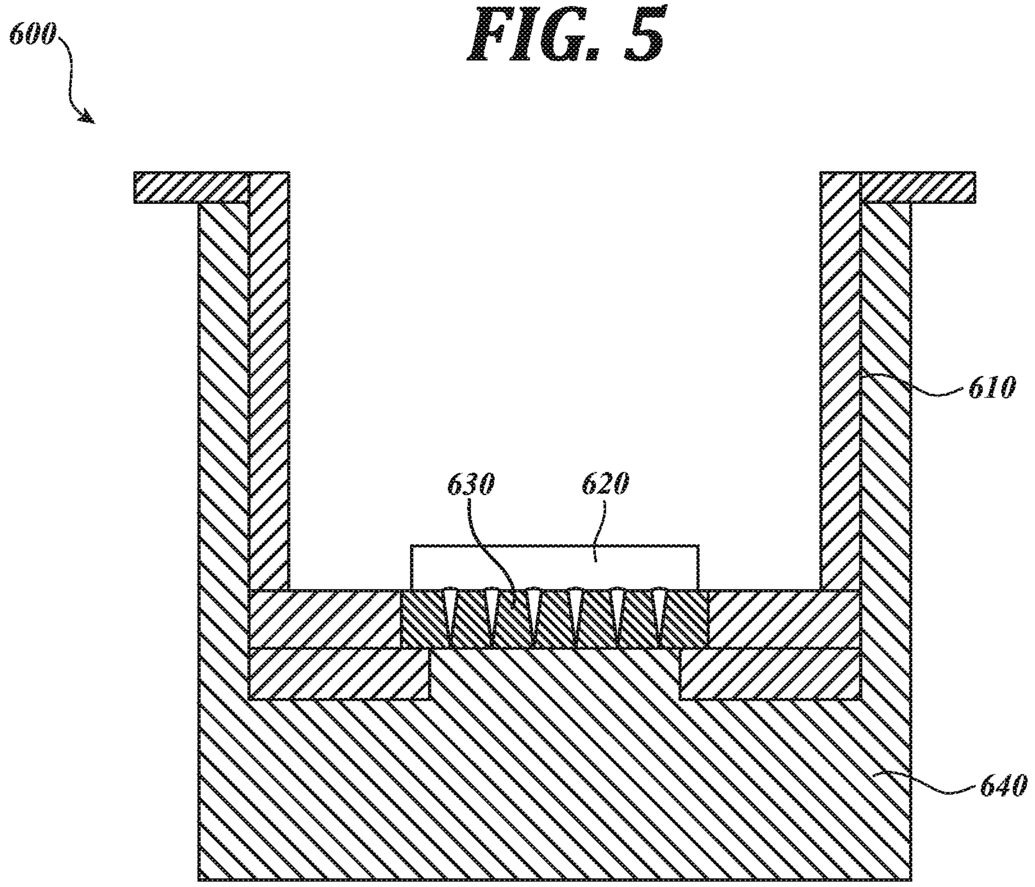
FIG. 6 illustrates an example transdural delivery process using a device according to an embodiment of the present disclosure.

Further, the process of testing the microneedle's ability to deliver dexamethasone into a solution is described herein. Two testing methods were introduced: one the array is completely submerged into a solution, which allows for degradation from all sides and gives insight into the total loading capacity of the microneedle arrays. The second experimental design includes a transwell insert, as shown in FIG. 6, that simulates the microneedles' transdural drug delivery aspect. In this setup, a piece of collagen dural substitute is placed inside in a custom well-insert, and the microneedles are pressed into this dura. The solution below these inserts is then sampled, and the transdural delivery can be accurately quantified using the methods described herein.

Figure 4A:
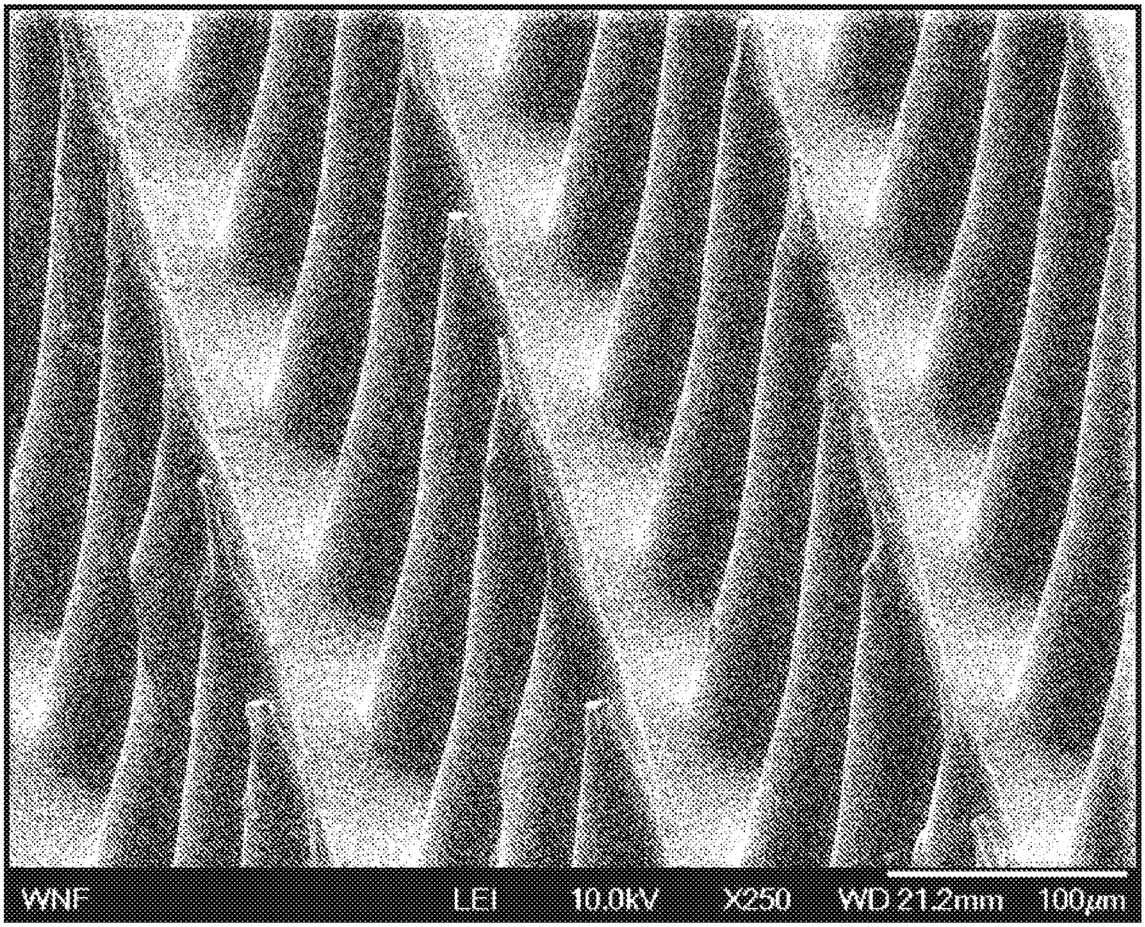
FIGS. 4A and 4B are SEM images of an example device, in accordance with the present technology.
Figure 4B:
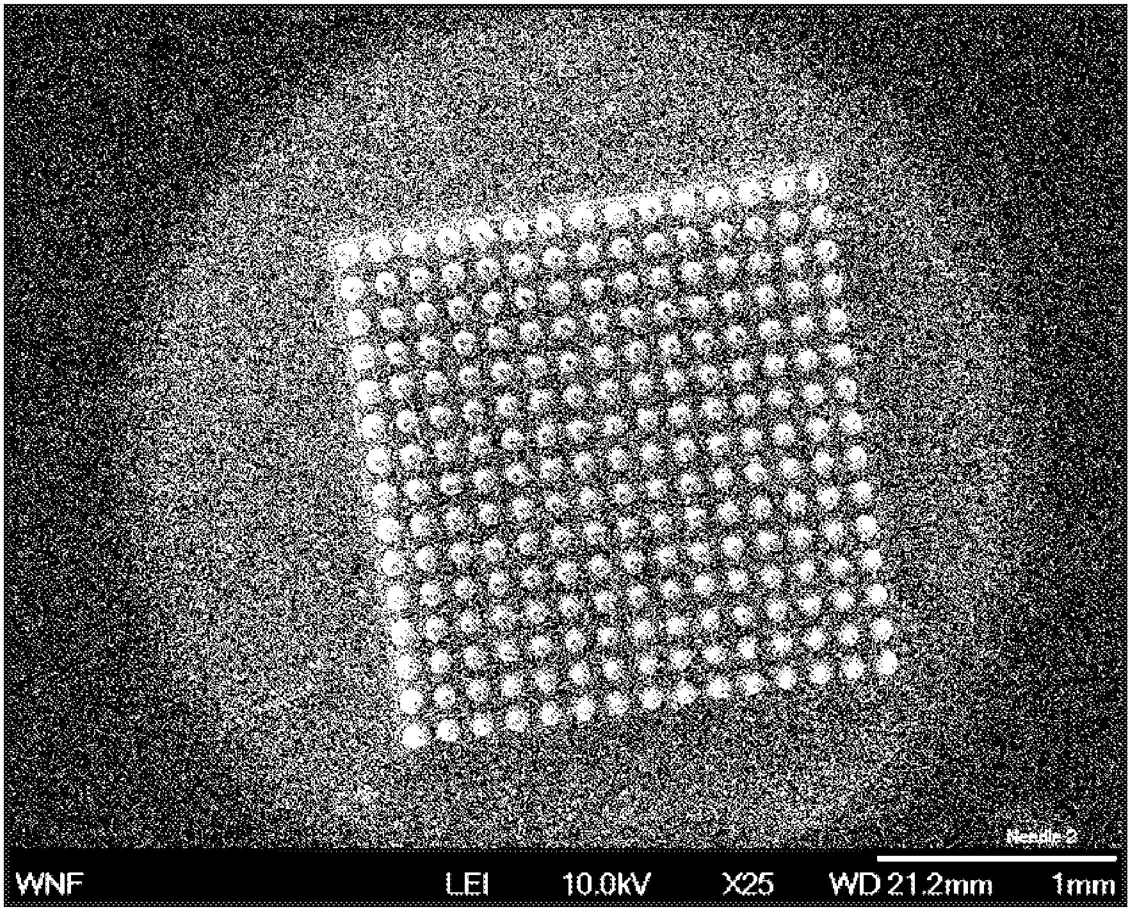

FIGS. 4A and 4B are SEM images of an example device, in accordance with the present technology. Microneedles were manufactured based on the process illustrated in FIGS. 2A-2D, and FIGS. 3A-3C. Microneedle arrays were placed into a 1.5 mL Eppendorf tube with 1 mL of PBS. Tubes were then placed in a holder in an incubator at 37.8° C. for 24 hours. At the 30-minute, 1 hour, 4 hour, and 24-hour time point, tubes were removed from the incubator, and the entire 1 mL content was transferred using a pipettor to new Eppendorf tubes. PBS was replenished, and tubes were placed back into the incubator. The tubes of PBS solution that were removed were then placed into a refrigerator until all samples were collected. After the 24-hour time point, all samples were filtered through a 0.2 μm PVDF filter before being added to 1.5 mL autosampler vials. Samples were then quantified using the HPLC-MS method.

Figure 5:
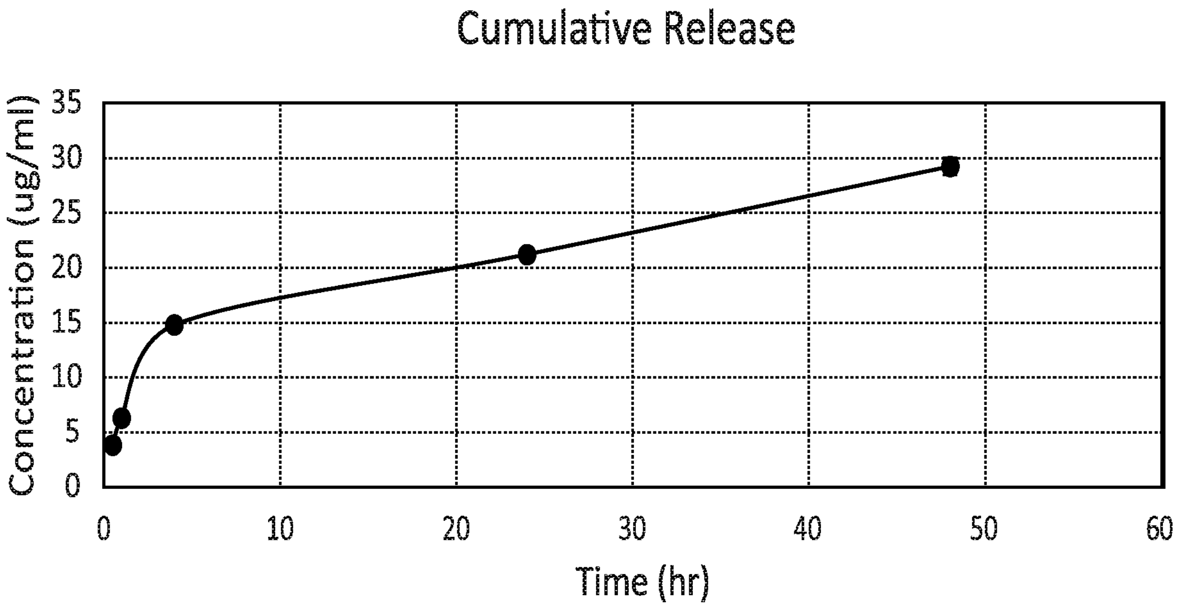
FIG. 5 is a graph of the cumulative release of a drug using a device, according to an embodiment of the present disclosure, over time, in accordance with the present technology.

FIG. 5 is a graph of the cumulative release of a drug over time, in accordance with the present technology. On the horizontal axis is the time in hours. On the vertical axis is the concentration in μg/mL. As shown, the microneedles sustained a controlled release over 48 hours. The arrays released 30% of their loading capacity and surpassed the 8 μg/mL goal. With the arrays being able to encapsulate and exceed the target range, new experimental method was introduced to better replicate the microneedle arrays' transdural delivery.

FIG. 6 is an example transdural delivery process, in accordance with the present technology. In some embodiments, the transdural delivery 600 includes a transwell insert 610 to hold an artificial dura 620. The device (also called "microneedles") 620 may sit on top of the artificial dura 620 and pierce the dura 620. The artificial dura 630 may sit on top of a 12-well plate of PBS/cell media 640. In some embodiments, the transwell insert 610 further includes one or more locking mechanisms.

To simulate the transdural delivery 600 of the microneedles 620 more accurately, a novel transwell insert 610 may be used. This transwell insert 610 may be designed and printed with a 3D printer using PLA. A collagen dural substitute 630 may be glued into these inserts 610, which allow for suspension directly above the solution in a 12-well plate 640. The microneedles 630 can then be pressed into the dura from above, replicating the insertion into the actual dura and the delivery of a drug, such as dexamethasone, into the subdural space.

In one embodiment, the experiment was done using 12 well plates 640. Each well was filled with 1.5 mL of PBS. Microneedles were manufactured in the method described herein. A 1 cm×1 cm square of the dural substitute 630 was cut and glued into the transwell inserts 610 using cyanoacrylate. The glue was allowed to cure for 5 minutes before the dura was hydrated using 1 mL of PBS. The PBS was allowed to hydrate for 5 minutes. The microneedle arrays 620 were then placed onto the dura 630 and, using thumb pressure, pressed into the dura 630. The well inserts 610 were then placed into the 12-well plates 640. The lid was placed on top, and the plates were put into the incubator for 24 hours. At the 30 minutes, 1 hour, 4 hours, and 24 hours' time points, the plates were removed from the incubator. All 1.5 mL of PBS was removed and stored in separate Eppendorf tubes. The PBS was replenished, and the plates were returned to the incubator until the next time point. The tubes of PBS taken from the plates were stored in the refrigerator until the 24 hours of release were complete. Each sample was filtered using a 0.2 μm PVDF filter before being added to autosampler vials. The samples were then quantified using the methods described herein.

To fix the issue of the microneedles not staying within the dura, a locking mechanism was introduced. In some embodiments, the locking mechanism is a small plate that can be 3D printed and pressed into the well insert after the array was placed. This plate stayed in place due to friction for the duration of the experiment.

Figure 7A:
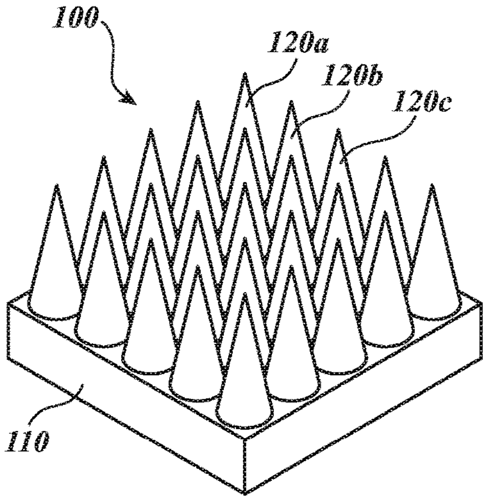
FIGS. 7A-7D are example configurations of a device in accordance with the present technology.
Figure 7B:
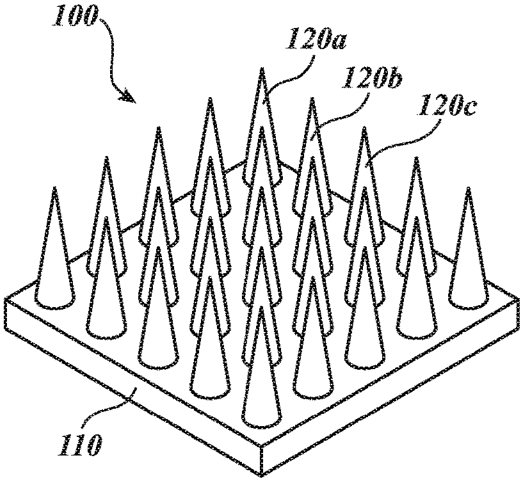
Figure 7C:
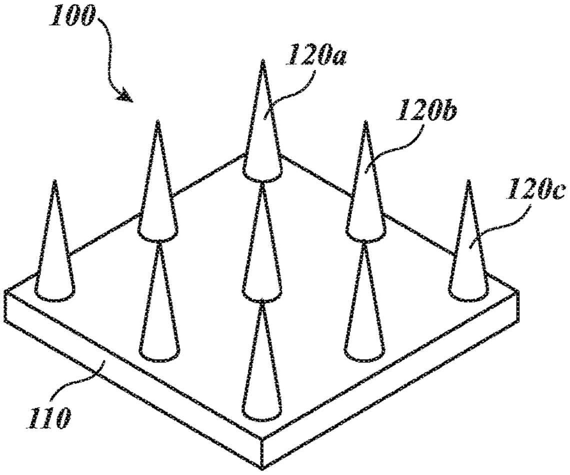

FIGS. 7A-7D are example configurations of a device in accordance with the present technology. Each of FIG. 7A-7C represents 10 mm of an example device 100. At times, the microneedle arrays had difficulties piercing the dura, with very little penetration for the 300 μm needles. To improve this, the design was altered so that the needles ranged from 0.5 mm to 5 mm. Each configuration was tested for its ability to pierce the dura. In some embodiments, the needles are 4 mm. Another issue arose when placing the needles into the dura; the arrays quickly pulled themselves out of the dura and did not remain inside the dura for the duration of the test.

One of the most significant issues found with the microneedle arrays was the "bed of nails" phenomenon, where individual needles would pierce when tested, but the entire array would not pierce. The needles were too close together and did not have the height to pierce through the dura properly. To reduce this effect, the design of the array was changed to be much larger and more spread apart. In some embodiments, the length across the entire dural substrate ranges from 1-6 mm. It was found that 4 mm was the ideal length to cross the entire dural substitute. After multiple design alterations, the one that provided the best results was an array with 4 mm microneedles spread out over a 10 mm×10 mm surface, as shown in FIG. 7C. When tested on only the dural substitute, the needles pierced and left indents in the dura. The arrays still slowly pushed out of the dura, so the well lock was used to hold them in place during the experiment.

FIG. 7A illustrates an embodiment of the device 100, in accordance with the present technology. In some embodiments, the base 110 is 2 mm thick. In some embodiments, the microneedles 120*a*, 120*b*, 120*c* are 2 mm in height.

FIG. 7B illustrates an embodiment of the device 100, in accordance with the present technology. In some embodiments, the base 110 is 0.5 mm thick. In some embodiments, the microneedles 120*a*, 120*b*, 120*c* are 4 mm in height. In some embodiments, the 4 mm needles are densely packed in the 10 mm of space.

FIG. 7C illustrates an embodiment of the device 100, in accordance with the present technology. In some embodiments, the microneedles 120*a*, 120*b*, 120*c* are 4 mm in height, and sparsely distributed. This configuration yielded the best results for piercing the dura and administering the drug.

Figure 7D:
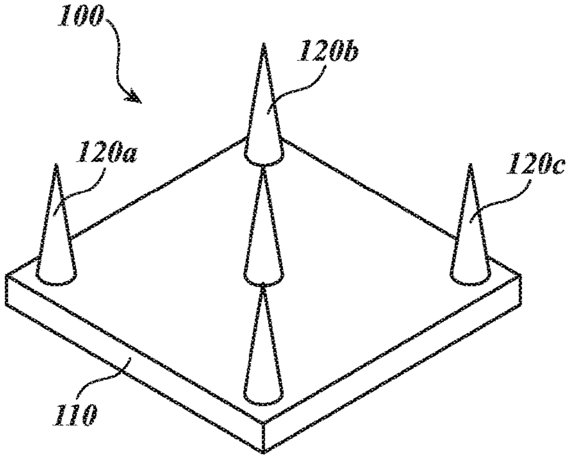

FIG. 7D illustrates an embodiment of the device 100, in accordance with the present technology. In some embodiments, the microneedles 120*a*, 120*b*, 120*c* are 4 mm in height and are dispersed on the base 110 in an "X" configuration.

After finding an appropriate configuration for the microneedles, the delivery of a drug, such as dexamethasone, was tested.

TABLE 3

Description of variables used for transdural drug delivery experiments.

| Variable Name | Description |
|---|---|
| Drug Needle (DN) | Dexamethasone loaded microneedle array |
| Drug Gel (DG) | Dexamethasone-loaded gel without needles placed on top of the dura. Dexamethasone and polymer volumes are equal. |
| Blank Needle (BN) | Microneedle array without dexamethasone. |
| Blank Gel (BG) | Polymer gel without needles. |
| Epidural (ED) | Dexamethasone solution that was pipette on the top of the dura. Volume and dexamethasone concentrations were the same. |
| Subdural (SD) | Dexamethasone solution pipetted into the well. Same volume and concentration as arrays. |
| Control | Only PBS in the wells, no treatment. |

Figure 9:
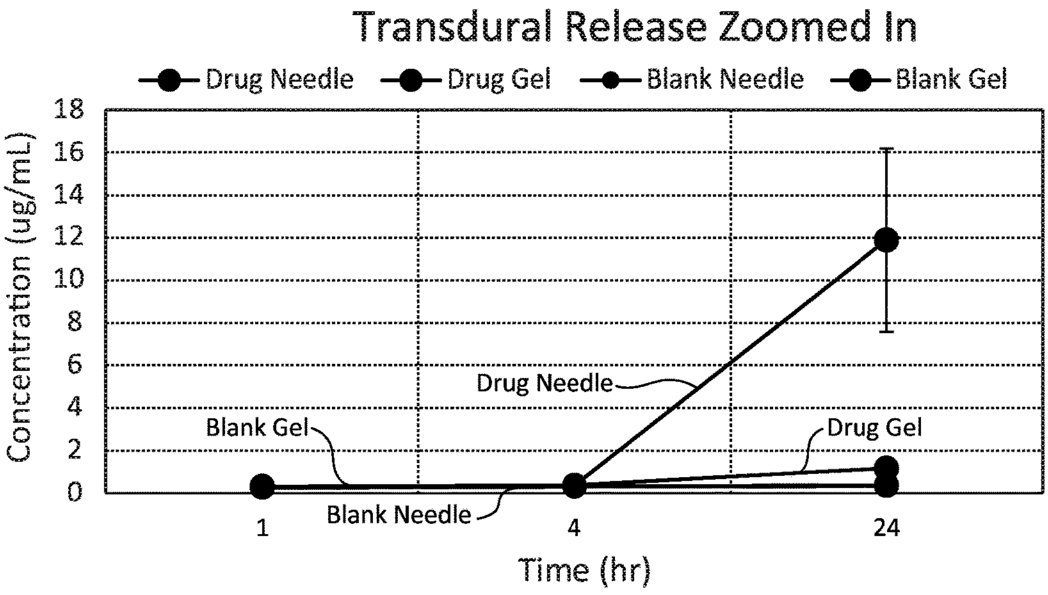
FIG. 9 is an enlarged image of the graph in FIG. 8, showing the transdural release of the drug using the device, according to an embodiment of the present disclosure, in comparison with other delivery mechanisms.

Results of the microneedle study were mixed. Improvements in needle stability with increased sizes were seen but still could not overcome the "bed of nails" effect. Although the increased dimensions improved the rigidity, the needles still failed to pierce the dura completely and were still pushed out of the dura over time. The results did show that some payload was delivered across the dura within the therapeutic target, but only after 24 hours, as shown in FIG. 9. One issue with the experimental system is that the collagen dural substitute is much more fibrous than biological dura and that the needles may perform better in ex-vivo dura samples.

Figure 8:
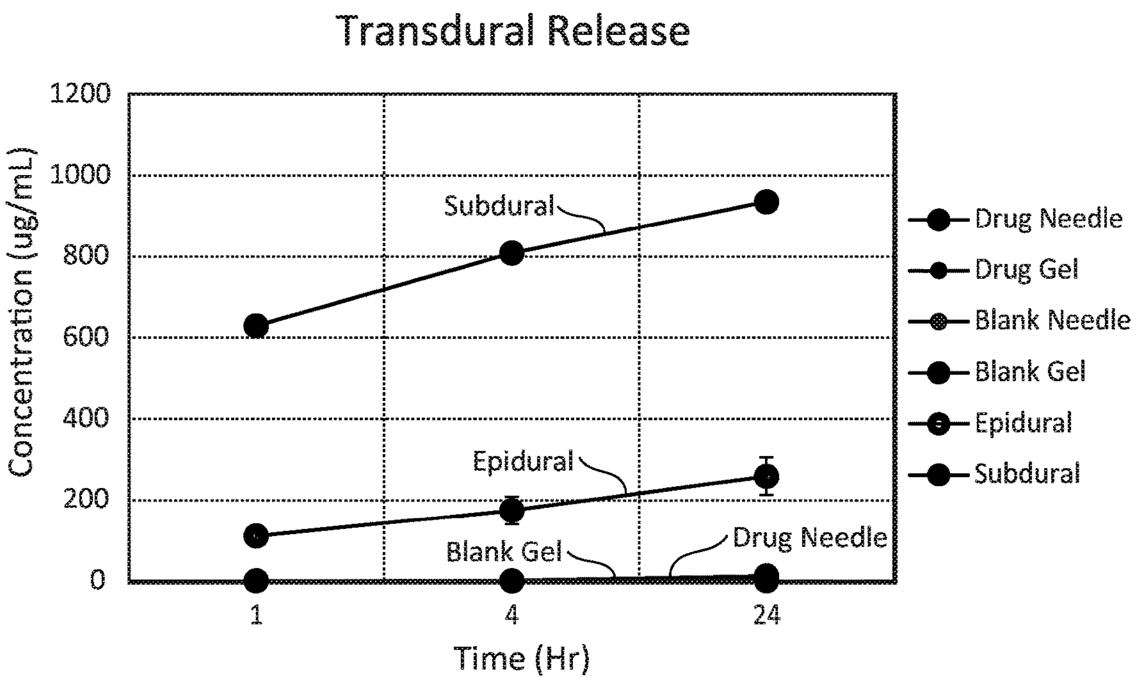
FIG. 8 is a graph of transdural release of a drug using device, according to an embodiment of the present disclosure, in comparison with other delivery mechanisms.

FIG. 8 is a graph of the transdural release of a device in comparison with other delivery mechanisms, in accordance with the present technology. FIG. 9 is an enlarged image of the graph in FIG. 8, showing the transdural release of a device in comparison with other delivery mechanisms, in accordance with the present technology. On the horizontal axis in the time in hours. On the vertical axis is the concentration in μg/mL. Plotted are the transdural releases of the drug needle, drug gel, a blank needle, a blank gel, and an epidermal and subdural release for comparison.

While the subdural and epidural methods resulted in higher concentrations as shown in FIG. 8, the drug needle was able to deliver some payload into the dura as shown in FIG. 9.

In some embodiments, the device may be used as a method of treating a subject having a neurological injury to prevent or mitigate secondary injury, the method including applying a microneedle device to dura of the subject at or adjacent to a site of the neurological injury, the microneedle device including a base, and a plurality of microneedles protruding from the base, the microneedles including a biocompatible and biodegradable matrix, and a neurologically active ingredient disposed within the matrix, where applying the microneedle device to the dura pierces the dura, thereby releasing the neurologically active ingredient to injured neural tissue of the subject. In some embodiments, the neurologically active ingredient has an anti-inflammatory effect on the injured neural tissue. In some embodiments, the anti-inflammatory effect is determined by decrease in expression of inflammatory cytokines selected from the group consisting of IL1a, IL1b, TNFα, and combinations thereof after the application of the microneedle device.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

From the foregoing, it will be appreciated that, although specific embodiments of the invention have been described herein for purposes of illustration, various modifications may be made without deviating from the spirit and scope of the invention.

Accordingly, the invention is not limited except as by the appended claims.

The invention claimed is:

1. A device for delivering a neurologically active ingredient to a dura of a subject, the device comprising:

a base comprising a first surface that is adjacent to a surface of the dura;

a plurality of microneedles protruding from the first surface of the base and into the dura, wherein each of the microneedles comprise:

a biocompatible and biodegradable matrix; and a neurologically active ingredient disposed within the matrix; and a locking mechanism, wherein the density of microneedles on the first surface of the base ranges from 5 microneedles to 9 microneedles per 100 $mm^2$, and wherein the distance between any two adjacent microneedle centers is from 4.5 mm to 13 mm, and wherein the plurality of microneedles have a height ranging from 500 μm to 5 mm.

2. The device of claim 1, wherein the neurologically active ingredient is an anti-inflammatory compound.

3. The device of claim 1, wherein the neurologically active ingredient is a corticosteroid.

4. The device of claim 1, wherein the neurologically active ingredient is selected from the group consisting of IL-10, dexamethasone, methylprednisolone, hydrocortisone, riluzole, minocycline, brain derived neurotrophic factor (BDNF), nerve growth factor (NGF), neurotrophin-3 (NT-3), and combinations thereof.

5. The device of claim 1, wherein the neurologically active ingredient is dexamethasone.

6. The device of claim 1, wherein the matrix comprises a polymeric material selected from the group consisting of poly(ethylene glycol) diacrylate (PEG-DA), polyvinylpyrrolidone (PVP), polylactic co-glycolic acid (PLGA), poly caprolactone (PCL), polyvinhyl alcohol, polypyrrole, poly (3,4-ethylenedioxythiophene) polystyrene sulfonate (PEDOT), and combinations thereof.

7. The device of claim 1, wherein a weight:weight ratio of the neurologically active ingredient to the matrix is in a range of between about 80:15 and 95:5.

8. The device of claim 1, wherein the plurality of microneedles is configured to pierce the dura when applied thereto.

9. The device of claim 1, wherein a portion of the plurality of microneedles is shaped to penetrate the dura when the device is placed in contact with the dura.

10. The device of claim 1, wherein microneedles of the plurality of microneedles have a length extending from the base in a range of about 50 μm to about 2000 μm.

11. The device of claim 1, wherein microneedles of the plurality of microneedles are disposed on the base in an array.

12. A method of making the microneedle device of claim 1, the method comprising:

disposing a neurologically active ingredient and a monomer mixture in a microneedle mold; and polymerizing the monomer mixture in the microneedle mold to provide microneedles comprising a biocompatible and biodegradable matrix encasing the neurologically active ingredient.

13. The method of claim 12, further comprising removing the microneedles from the microneedle mold.

14. The method of claim 12, further comprising preparing the microneedle mold through additive manufacturing.

15. The method of claim 12, wherein the additive manufacturing comprising:

additively manufacturing a negative mold shaped to form a negative space of the microneedle mold;

disposing the negative mold in an elastomer to form the microneedle mold.

16. The method of claim 12, wherein the microneedle mold defines a plurality of structures shaped to form the plurality of microneedles.

17. The method of claim 16, wherein the plurality of structures define a depth in a range of about 50 μm to about 2000 μm.

18. The method of claim 12, wherein the monomer mixture comprises monomers selected from the group consisting of ethylene glycol, acrylic acid, vinylpyrrolidone, and combinations thereof.

19. The method of claim 12, wherein a weight:weight ratio of the neurologically active ingredient to monomers in the monomer mixture is in a range of between 80:15 and 95:5.

20. A method of treating a subject having a neurological injury to prevent or mitigate secondary injury, the method comprising:

applying the microneedle device of claim 1 to dura of the subject at or adjacent to a site of the neurological injury, the microneedle device comprising:

a base; and a plurality of microneedles protruding from the base, the microneedles comprising:

a biocompatible and biodegradable matrix; and a neurologically active ingredient disposed within the matrix, wherein applying the microneedle device to the dura pierces the dura, thereby releasing the neurologically active ingredient to injured neural tissue of the subject.

21. The method of claim 20, wherein the neurologically active ingredient has an anti-inflammatory effect on the injured neural tissue.

22. The method of claim 21, wherein the anti-inflammatory effect is determined by decrease in expression of inflammatory cytokines selected from the group consisting of IL Ia, IL Ib, TNFα, and combinations thereof after the application of the microneedle device.

23. The device of claim 1, wherein the plurality of microneedles are about 4 mm in height.

24. The device of claim 1, wherein the distance between any two adjacent microneedle centers is from 4.5 mm to 9 mm.

* * * * *